(12) United States Patent
Graf

(10) Patent No.: US 6,419,706 B1
(45) Date of Patent: Jul. 16, 2002

(54) PARTIAL DISC PROSTHESIS

(75) Inventor: Henry Graf, Lyons (FR)

(73) Assignee: Sofamor S.N.C., Cedex (FR)

( * ) Notice: Subject to any disclaimer, the term of this patent is extended or adjusted under 35 U.S.C. 154(b) by 0 days.

(21) Appl. No.: 09/581,884

(22) PCT Filed: Dec. 18, 1998

(86) PCT No.: PCT/FR98/02798

§ 371 (c)(1),
(2), (4) Date: Nov. 2, 2000

(87) PCT Pub. No.: WO99/32054

PCT Pub. Date: Jul. 1, 1999

(30) Foreign Application Priority Data

Dec. 19, 1997 (FR) .............................. 97 16548
Mar. 12, 1998 (FR) .............................. 98 03268

(51) Int. Cl.[7] .................................. A61F 2/44
(52) U.S. Cl. .................................. 623/17.16
(58) Field of Search ............... 623/17.11–17.16

(56) References Cited

U.S. PATENT DOCUMENTS

| | | | | |
|---|---|---|---|---|
| 4,911,718 A | * | 3/1990 | Lee et al. ................. | 623/17.11 |
| 5,534,030 A | * | 7/1996 | Navarro et al. .......... | 623/17.11 |
| 5,556,431 A | * | 9/1996 | Buttner-Janz ............ | 623/17.11 |
| 5,616,142 A | | 4/1997 | Yuan et al. ................ | 606/61 |
| 5,658,335 A | * | 8/1997 | Allen ....................... | 623/17.11 |
| 5,674,294 A | * | 10/1997 | Bainville et al. ........ | 623/17.11 |
| 5,702,450 A | * | 12/1997 | Bisserie ................... | 623/17.11 |
| 5,865,845 A | * | 2/1999 | Thalgott ................... | 623/17.11 |
| 5,865,847 A | * | 2/1999 | Kohrs et al. ............. | 623/17.11 |
| 5,976,187 A | * | 11/1999 | Richelsoph ............... | 623/17.11 |
| 6,224,631 B1 | * | 5/2001 | Kohrs ....................... | 623/17.11 |
| 6,258,125 B1 | * | 7/2001 | Paul et al. ................ | 623/17.11 |

FOREIGN PATENT DOCUMENTS

| | | | | |
|---|---|---|---|---|
| DE | 4323595 C1 | 7/1993 | ............. | A61F/2/44 |
| EP | 0260044 A1 | 8/1987 | ............. | A61F/2/44 |
| EP | 0346269 A2 | 6/1989 | ............. | A61F/2/44 |
| EP | 0566810 A1 | 4/1992 | ............. | A61F/2/44 |
| EP | 0610837 A1 | 7/1994 | ............. | A61F/2/44 |
| WO | WO 90/11740 | 10/1990 | ............. | A61F/2/44 |
| WO | WO 95/00082 | 1/1995 | ............. | A61F/2/44 |
| WO | WO 95/15133 | 8/1995 | ............. | A61F/2/44 |
| WO | WO 97/15247 | 1/1997 | ............. | A61F/2/44 |
| WO | WO 97/31517 | 8/1997 | ............. | J16B/37/14 |

* cited by examiner

Primary Examiner—David H. Willse
Assistant Examiner—Suzette J. Jackson
(74) Attorney, Agent, or Firm—Woodard, Emhardt, Naughton Moriarty & McNett

(57) ABSTRACT

The invention concerns a prosthesis (2) designed to be inserted between two neighboring vertebrae, comprising a core (4) made of an elastic material and covered, over part of its periphery, with a rigid material coating (6) designed to be in contact with the two neighboring vertebrae. The core (4) comprises, in transverse cross-section, two end portions (8) linked by a median portion (12) and said coating includes two caps provided with a threading and covering at least partially the external periphery of the end portions (8), the distance separating the caps increasing towards the prosthesis front part.

19 Claims, 11 Drawing Sheets

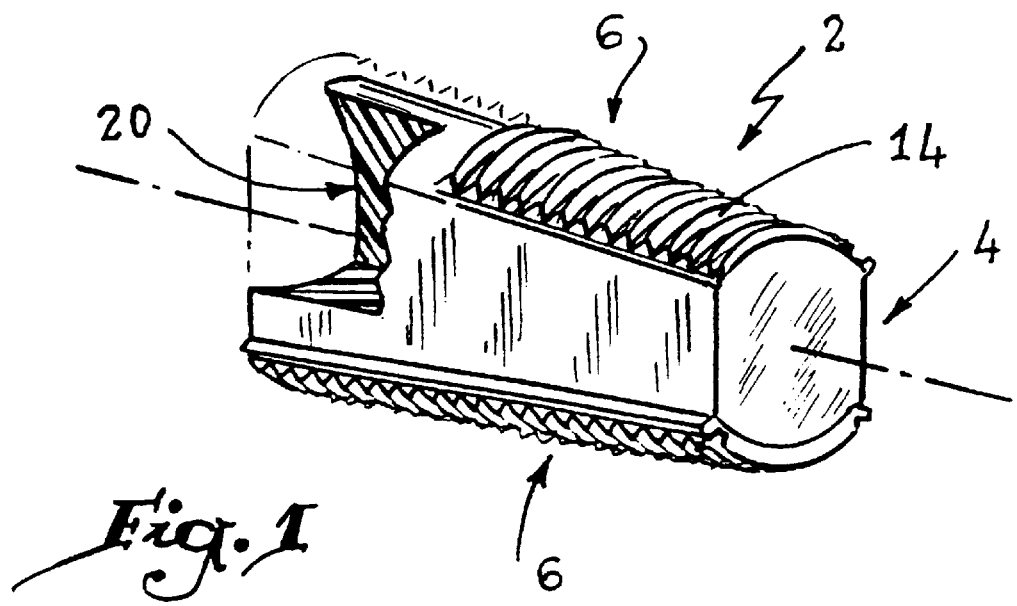
Fig. 1
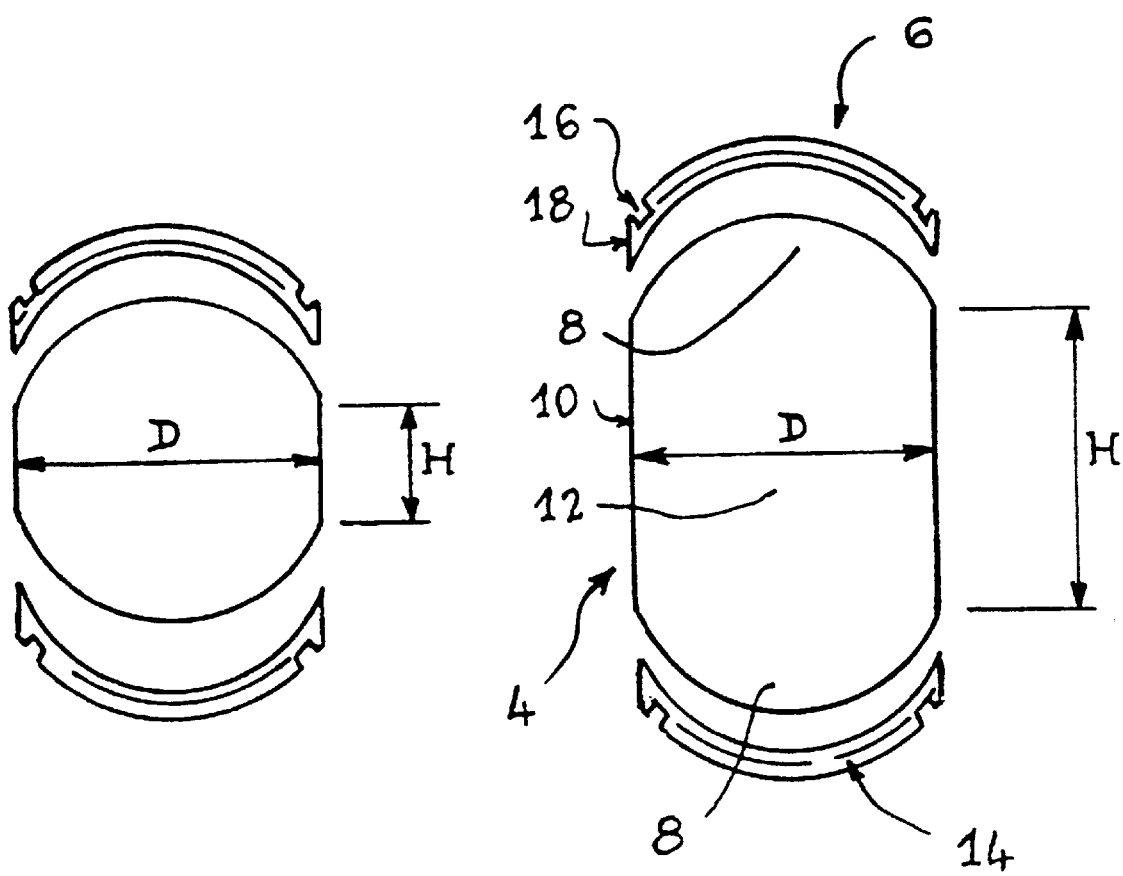
Fig. 2
Fig. 3

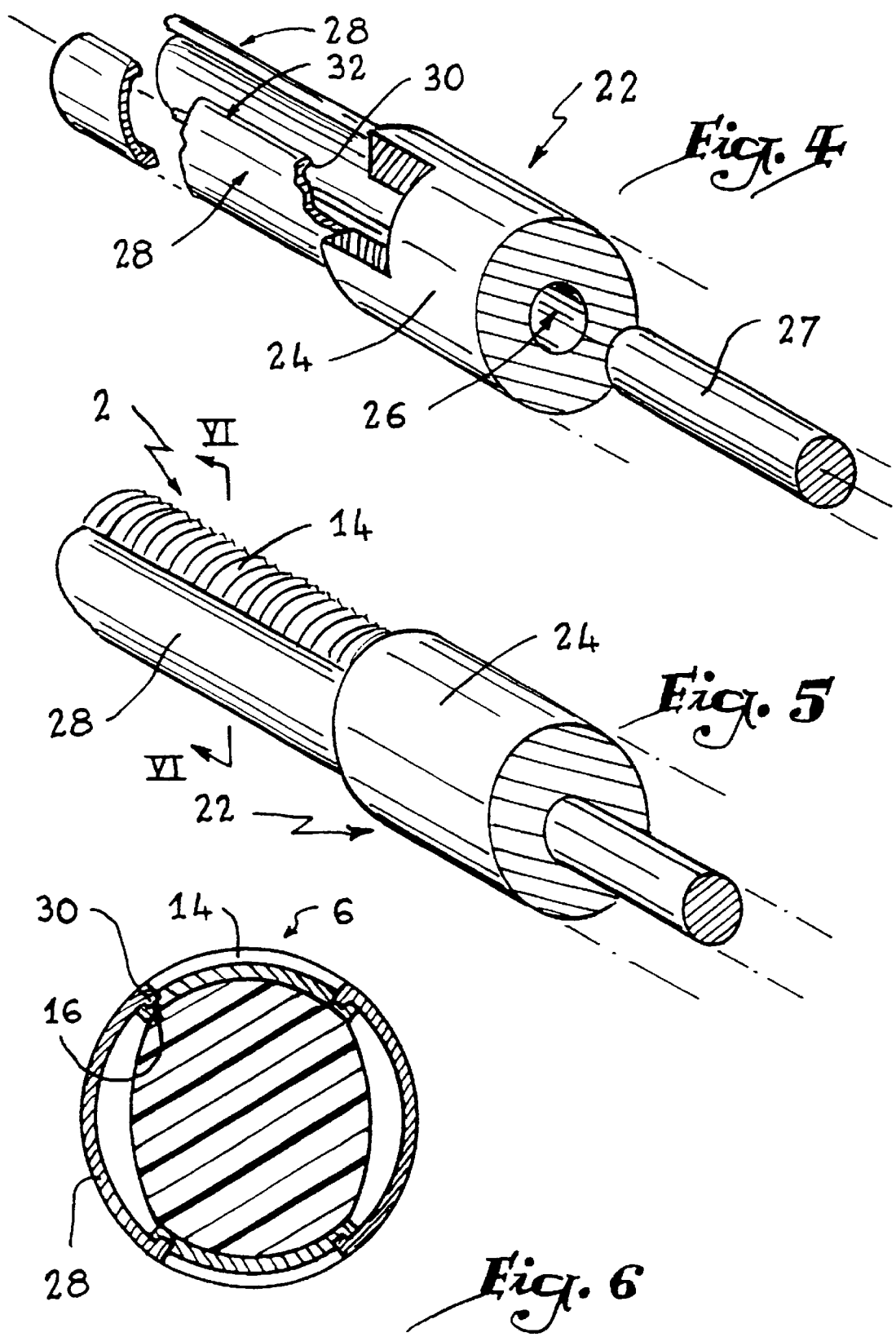

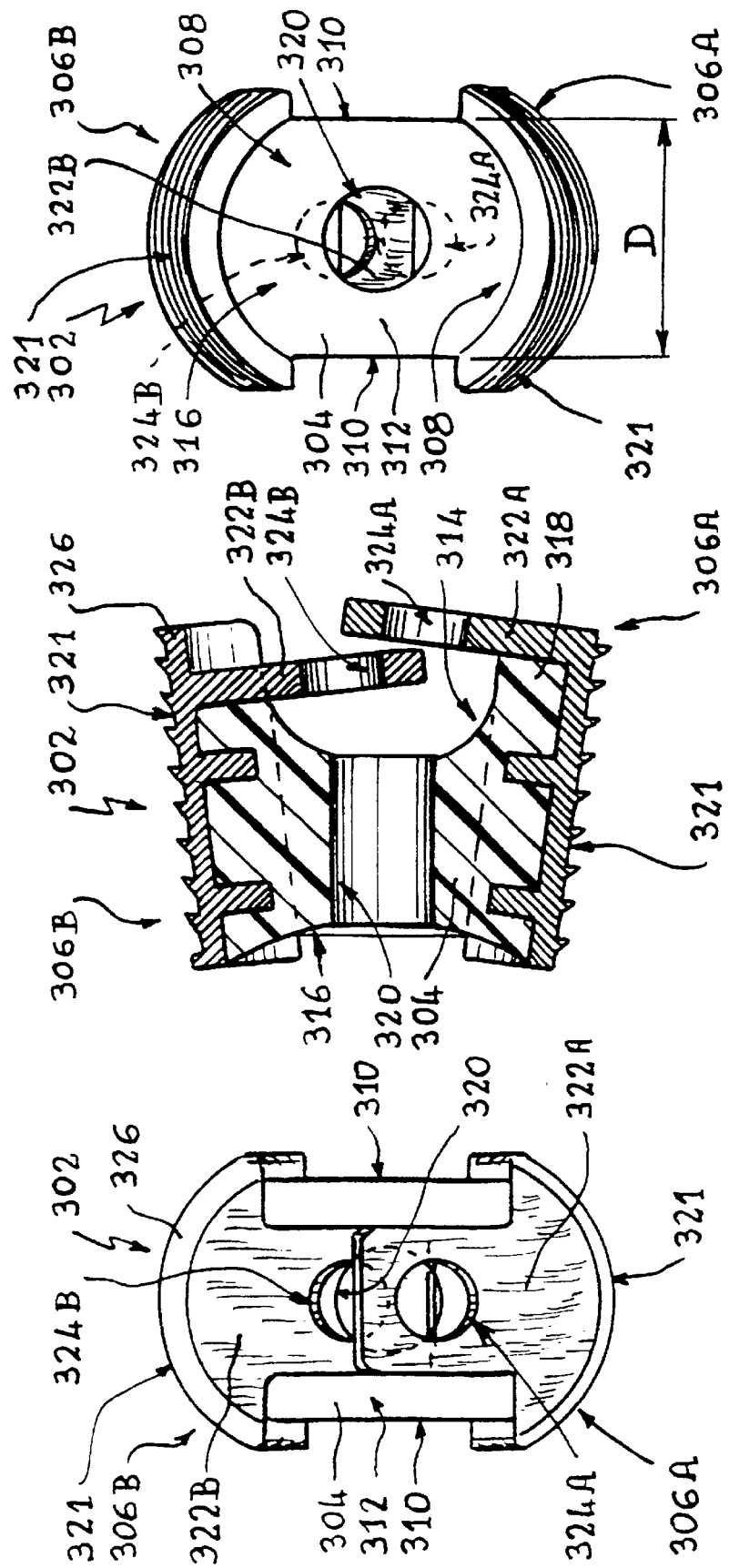

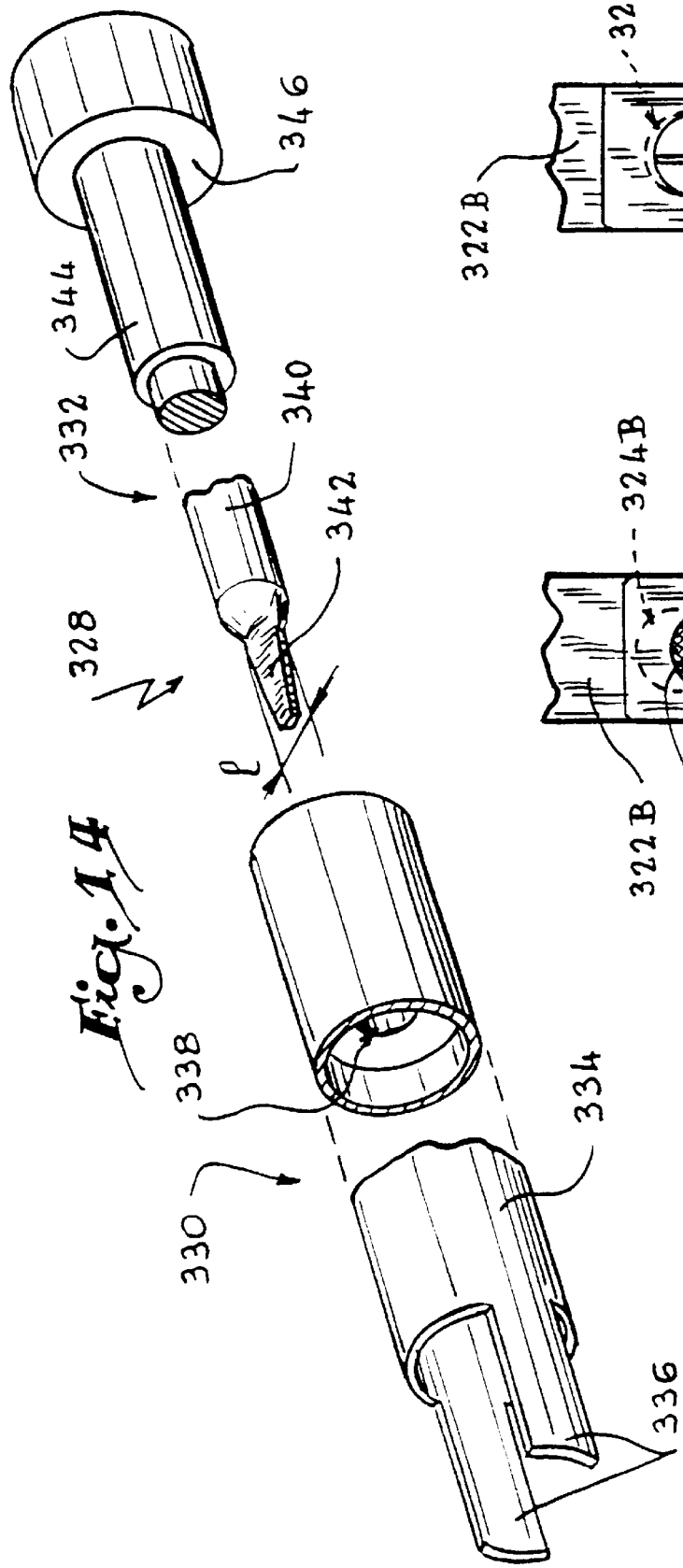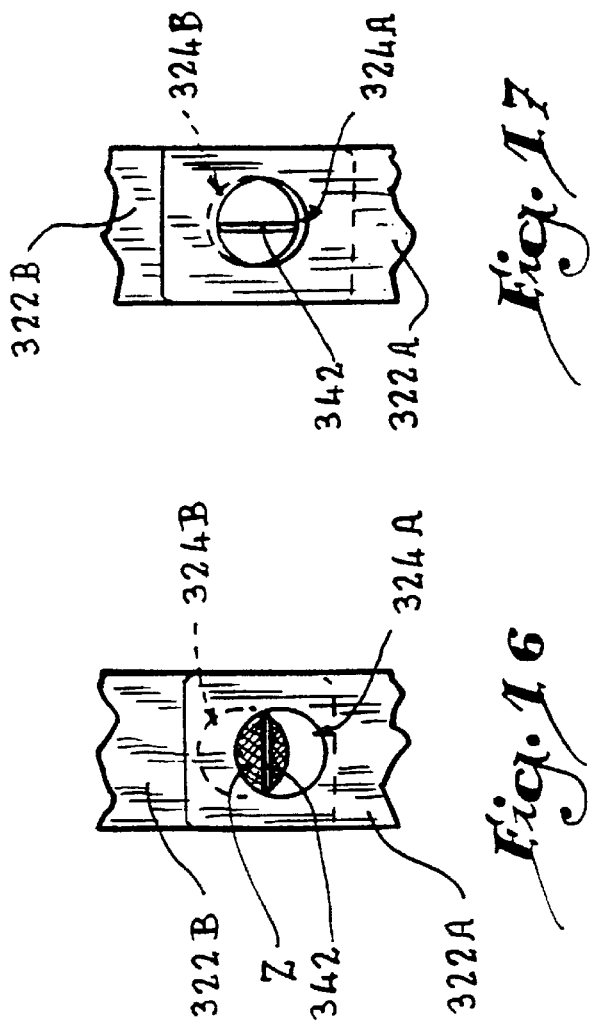

PARTIAL DISC PROSTHESIS

The present invention concerns a partial disc prosthesis.

Disc prostheses, which can be partial or total, are normally intended to replace all or part of an intervertebral disc when the latter has been destroyed by surgery or by disease.

A first type of disc prosthesis consists of a rigid cage which, for example, can be rectangular in cross section, and in which perforations are formed for receiving grafts which are intended to ensure satisfactory attachment of this cage with the two vertebrae between which it is to be inserted. This type of rigid cage, which is implanted in particular by impaction or screwing, has a disadvantage in that it leads to complete blocking of the two vertebrae between which the cage is arranged, and this limits the patient's freedom of movement.

An intervertebral disc prosthesis is also known from the document EP-A-0,346,269, which prosthesis is made up of a core of viscoelastic material interposed between two metal cover plates which, after they have been implanted, are intended to be in contact with the surface of the vertebrae. However, this type of prosthesis has a disadvantage which lies in particular in its lack of stability, so that there is a considerable risk of this prosthesis being ejected from the intervertebral space.

In order to overcome the abovementioned disadvantages of the prior art, the invention proposes a partial disc prosthesis which can be anterior or posterior, can be implanted easily in the intervertebral space, possesses satisfactory stability within this intervertebral space, and permits sufficient freedom of movement while at the same time guaranteeing a physiologically advantageous posture.

To this end, the invention relates to a partial disc prosthesis intended to be inserted between two adjacent vertebrae, of the type comprising a core made of an elastic material such as a silicone polymer or an elastomer, covered, over part of its periphery, by a casing made of a rigid material and intended to be in contact with the said two adjacent vertebrae, characterized in that the said core comprises, in cross section, two end portions connected by a middle portion, the said casing comprises two covers provided with a threading and covering, at least partially, the external periphery of the said end portions, and the distance separating the said covers increases towards the anterior part of the prosthesis.

The invention also proposes an implantation instrument for the prosthesis as described above, which instrument ensures easy implantation of the prosthesis, can be easily withdrawn once the prosthesis has been implanted, and makes it possible to preserve the integrity of the various organs around which this instrument is manoeuvred during all these operations.

To this end, the invention also relates to an implantation instrument for the prosthesis as described above, characterized in that it comprises a grip handle which is continued via means for securing the said prosthesis relative to the said instrument, in a transversely compressed state of the said prosthesis.

The invention will be described below with reference to the attached drawings which are given solely by way of non-limiting example and in which:

FIG. 1 is a perspective view, partially cut away, of a first embodiment of a disc prosthesis according to the invention;

FIGS. 2 and 3 are exploded end views, showing the front and rear parts, respectively, of the prosthesis shown in FIG. 1;

FIG. 4 is a diagrammatic perspective view, with part cut away, of an implantation instrument for the prosthesis shown in FIGS. 1 to 3;

FIG. 5 is a perspective view showing the prosthesis in FIGS. 1 to 3 engaged in the implantation instrument in FIG. 4

FIG. 6 is a cross section along the line VI—VI in FIG. 5;

FIG. 11 is an axial section of a fourth embodiment of a disc prosthesis according to the invention;

FIGS. 12 and 13 are end views representing the front and rear parts, respectively, of the prosthesis in FIG. 1;

FIG. 14 is a diagrammatic perspective view, with part cut away, of the various elements constituting an implantation instrument for the prosthesis shown in FIGS. 11 to 13;

FIG. 16 is a partial end view illustrating the tongues provided on the prosthesis shown in FIGS. 11 to 13, when the prosthesis has been implanted;

FIG. 17 is a view similar to FIG. 16, illustrating the respective position of the tongues of the prosthesis when withdrawn;

FIGS. 21 and 22 are cross sections along the line XXI—XXI in FIG. 18, in rest and compression positions, respectively, of the prosthesis in this FIG. 18;

Figure 7:
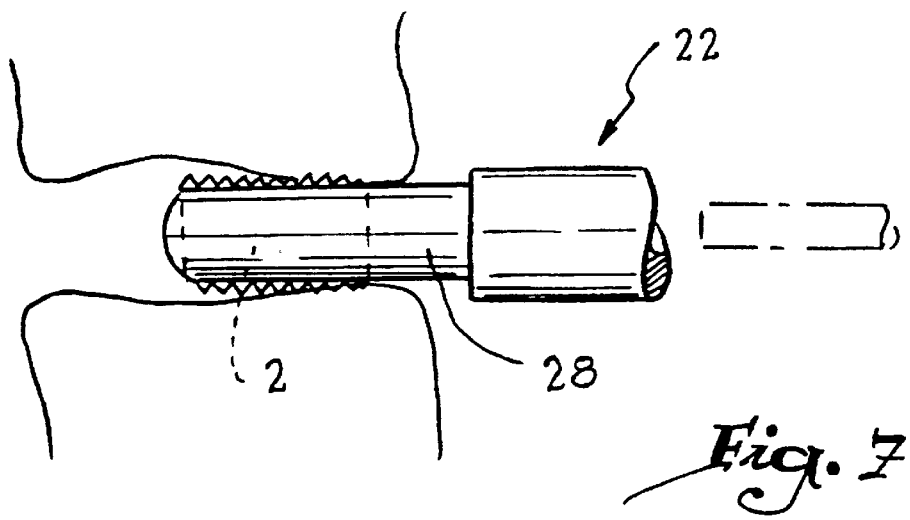
FIG. 7 is a diagrammatic view illustrating the implantation of the prosthesis in FIGS. 1 to 3.

As is shown in FIGS. 1 to 3, the disc prosthesis according to the invention, designated as a whole by reference number 2, comprises a core 4 whose outer surface is partially covered by means of two casings formed by covers 6. The core 4 is made of a biocompatible elastic material, for example a silicone polymer or a prestressed rubber. The covers 6 are made of a biocompatible rigid material, for example special steel, in particular titanium, and are attached to the core, for example, by a silicone adhesive or other adhesive.

As is shown in particular in FIGS. 2 and 3, the cross section of the core 4 is made up of two end portions 8 whose outer periphery describes an arc of a circle and which are connected via two flat surfaces 10 forming a middle part 12.

A cup-shaped recess 20 is formed in the front end of the core 4 and constitutes an incipient flexion means, as will be seen from the description which follows.

Each cover 6 is made in the form of a profiled part having, in cross section, the shape of an arc of a circle. These covers cover the whole of the outer periphery of the end portions 8 of the core 4, whereas the flat surfaces 10 are not covered. The outer surface of these covers is provided with a threading 14 intended to facilitate implantation of the prosthesis, as will be explained hereinafter.

The outer surface of the covers 6 also has irregularities, for example formed by embossing or sintering, which are intended to guarantee good stability of the prosthesis once it has been fitted. Axial slots 16 are additionally formed along the whole length of each cover, near each edge 18 of these covers.

It should be noted that the transverse dimension or width D of the end portions 8 is substantially constant along the whole length of the prosthesis, whereas the dimension or height H of the flat surfaces 10 connecting these end portions increases towards the front of the prosthesis, referring to the prosthesis once It has been fitted in a patient.

The distance separating the covers increases towards the front of the prosthesis. The distance separating the covers is intended to signify the maximum distance, in cross section, separating the respective zones of contact of the covers with the vertebrae, in the compressed position of the prosthesis.

By way of indication, the length of the prosthesis, namely the distance separating its front and rear ends, is of the order of 16 to 20 mm, for example, its minimum height H at the rear part of the prosthesis is of the order of 12 mm, while its maximum height H is of the order of 16 mm. The radius of curvature of the inner part of each cover is, for example, about 12 mm, and these covers extend about an angular sector of the order of 120° each. Finally, the thickness of the covers is, for example, about 2 mm.

FIG. 4 shows an instrument, designated as a whole by reference number 22, intended for implanting the prosthesis 2 within the intervertebral space of a patient. This instrument 22 comprises a cylindrical elongate handle 24 whose dimensions permit easy gripping by a surgeon. This handle 24 has a coaxial central orifice 26 running through it, the transverse dimensions of which are less than those of the rear part of the prosthesis 2. This orifice 26 permits the passage of a rod 27, as will be explained hereinafter.

The handle 24 ends with two tongues 28 which are symmetrical with each other and are each made in the form of a thin profiled part having the shape of an arc of a circle. These tongues have a radius of curvature similar to that of the covers 6 of the prosthesis and they extend about angular sectors whose value, added to that of the angular sectors of the covers 6, is slightly greater than 360°. Axial ribs 30 project inwards along the entire length of each tongue, at each of the edges 32 of these, as is shown in particular in FIG. 6. The transverse dimensions of these ribs are such that they are able to fit in the slots 16 formed in the covers 6.

The longitudinal dimension of the tongues 28 is similar to, or even very slightly greater than, that of the overall prosthesis 2.

FIGS. 5 and 6 show the prosthesis 2 engaged in the cylindrical volume defined by the tongues 28 of the implantation instrument 22. To fit the prosthesis, it is preferable first to engage the end of the ribs 30, opposite the handle 24, in the rear end of the slots 16. The front of the prosthesis is then compressed, for example manually, which is made possible both by the elastic nature of the core 4 and by the presence of the recess 20. Each rib 30 is then slid in a corresponding slot 16 until the rear end of the prosthesis 2 comes into abutment against the end of the handle 24 adjacent to the tongues 28.

Once fitted in this way, the prosthesis, maintained in a cylindrical shape, has undergone an overall reduction in its transverse dimensions as a result of the compression, which increases towards the front of the prosthesis. As is shown in particular in FIG. 6, the middle part 12 of the prosthesis is in particular subjected to stresses tending to direct its outer periphery towards the tongues 28 of the implantation instrument.

The unit made up of the compressed prosthesis and the tongues 28 of the implantation instrument has a generally cylindrical shape. As is shown in FIG. 7, the prosthesis 2 is fitted by screwing by means of the handle 4 of the implantation instrument 22. The threading 14 provided on the outer surface of the covers 6 is advantageous with regard to this operation.

The outer surface of the tongues 28 is advantageously smooth since the implantation instrument has to be withdrawn after fitting.

Figure 8:
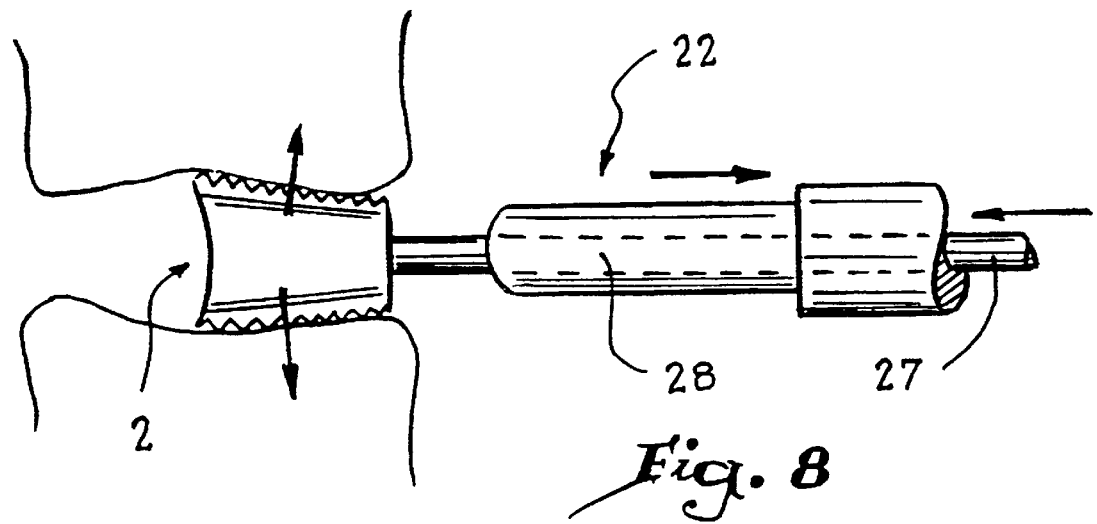
FIG. 8 is a diagrammatic view illustrating the disconnection of the implantation instrument in FIG. 4 from the prosthesis in FIGS. 1 to 3, after the prosthesis has been implanted.

FIG. 8 illustrates the operation consisting in withdrawing the implantation instrument 22 from the prosthesis 2. For this purpose, once the latter has been implanted in an appropriate position, it is held axially by means of the rod 27 penetrating into the orifice 26 formed in the handle 24. The ribs 30 of the tongues 28 are then slid backwards along the slots 16 of the covers 6. The prosthesis then recovers its original shape, as is shown in FIGS. 1 to 3, as a result of the nature of the prestressed material from which it is made.

FIGS. 5 to 8 illustrate the implantation of a prosthesis 2 intended to be placed to the rear of the intervertebral space and thereby constitute a posterior partial prosthesis. It is also possible to provide for this prosthesis 2 being positioned to the front of this intervertebral space. For this purpose, it is necessary to secure this prosthesis to the implantation instrument 22 by arranging its widened anterior part adjacent to the handle 24. This prosthesis is then implanted by screwing, as in the example described with reference to FIG. 7. This implantation is performed from the anterior part of the patient, for example by coelioscopy.

Figure 9:
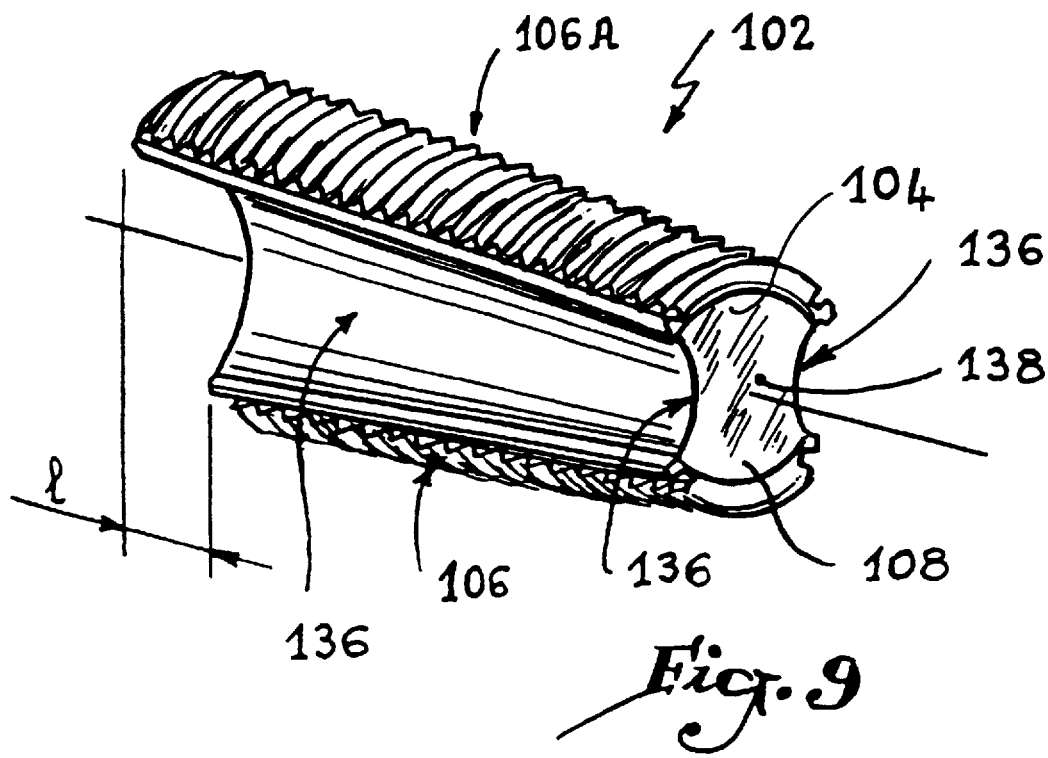
FIG. 9 is a diagrammatic perspective view of a prosthesis according to a second embodiment of the invention.

FIG. 9 shows a prosthesis 102 according to a second embodiment of the invention. The core 104 of this prosthesis comprises, like the core 4 described with reference to the preceding figures, two end portions 108 whose outer periphery describes an arc of a circle. These portions 108 are connected, no longer by flat surfaces, but by grooves 136, such that the end portions 108 constitute bulged portions connected by way of a middle part in the form of a neck 138. Each end portion 108 is covered by covers 106 forming a casing, of which one 106A extends longitudinally beyond the front end of the core 104, by a length 1. This cover 106A is intended to constitute the upper cover once the prosthesis has been implanted. The upper cover 106A projects relative to the front part of the core 104 by several millimetres or so.

The other component elements of this prosthesis 102 which are not discussed in the present description are identical to those of the prosthesis 2 described above.

Figure 10:
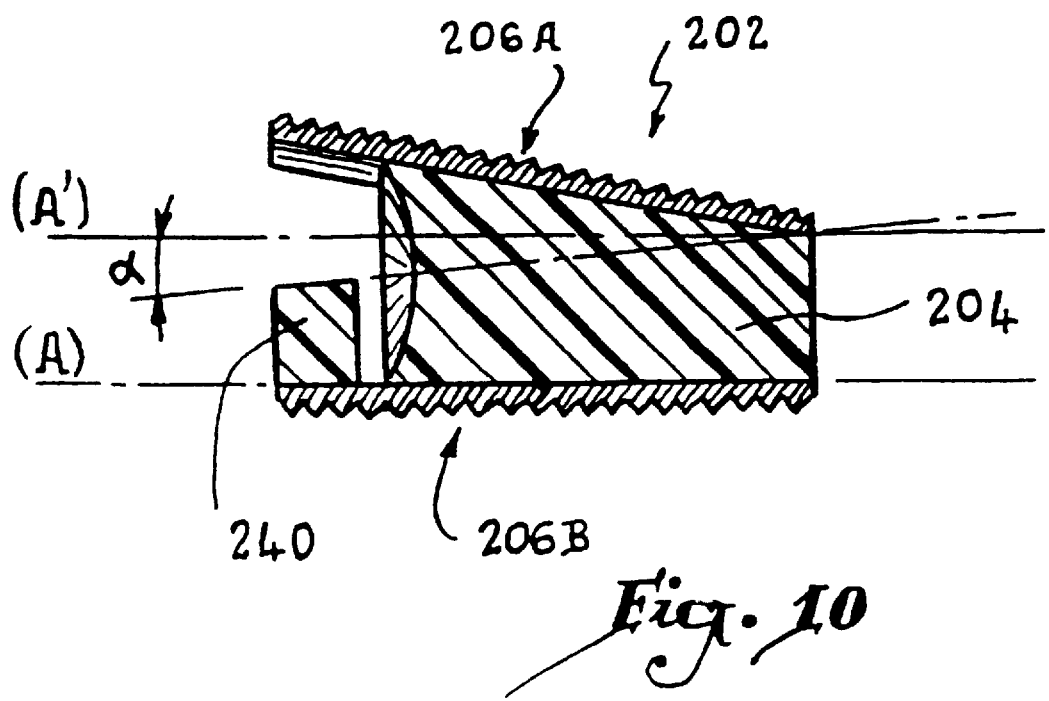
FIG. 10 is an axial section of a prosthesis according to a third embodiment of the invention.

FIG. 10 shows a prosthesis 202 according to a third embodiment of the invention.

This prosthesis 202 has two casings formed by covers 206A and 206B, upper and lower respectively, of equivalent axial dimensions.

The upper cover 206A projects beyond the front end of the core 204, in a similar manner to the prosthesis 102.

An abutment 240 projects from the lower cover 206B in the direction towards the upper cover 206A. The dimensions of this abutment are such that it limits the movement of inclination of the upper cover 206A to a defined value relative to an axis (A') parallel to the axis (A) of the lower cover. For example, the maximum inclination of the upper cover 206A can be limited to about 5° (angle α) downwards relative to the axis (A').

The abutment 240 is made of a material analogous to that of the core 204 and can be made in one piece with the latter.

The elements of this prosthesis which are not described are analogous to those of the prosthesis 102.

It is possible for a recess analogous to the recess 20 to be formed in the rear part of the prosthesis according to the invention. However, this recess must then have substantially smaller dimensions than the recess 20 so that preferential flexion is obtained in the front part of the prosthesis.

FIGS. 11 to 13 show a fourth embodiment of a partial disc prosthesis according to the invention, designated in general by reference number 302. This prosthesis comprises a core 304 made of a biocompatible elastic material, for example a silicone polymer or a prestressed rubber, the outer surface of which core 304 is partially covered by two covers 306A, 306B forming a casing. These covers are made of a biocompatible rigid material, for example a special steel, in particular titanium, and are attached to the core 304 by a silicone adhesive, for example.

As is shown in particular in FIGS. 12 and 13, the cross section of the core 304 is made up of two end portions 308 whose outer periphery describes an arc of a circle, and which are connected by two flat surfaces 310 forming a middle part 312.

The transverse dimension or width D of the end portions 308 is substantially constant along the whole length of the prosthesis 302, while the dimension or height H of the flat surfaces 310 connecting the end portions increases towards the front of the prosthesis, referring to the prosthesis when it has been implanted in the body of a patient. The core 304 is provided with first and second recesses 314, 316, also termed the anterior and posterior recesses. It should be noted that the anterior recess 314 has greater axial dimensions and a smaller radius of curvature than those of the posterior recess 316.

These cup-shaped recesses 314, 316 constitute incipient flexion means, their respective dimensions resulting in preferential flexion towards the front. The anterior recess 314 is continued, at one of its ends, via an extension 318 of the core 304, so that one of the end portions 308 has longitudinal dimensions greater than those facing it.

The prosthesis 302 has a longitudinal orifice 318 running through it, intended for the passage of a rod of an implantation instrument, as will be explained hereinafter.

Each cover 306 is made in the form of a profiled part having, in cross section, the shape of an arc of a circle. These covers cover the whole of the outer periphery of the end portions 308 of the core 304, whereas the flat surfaces 310 are not covered. The outer surface of these covers is provided with a threading 321 intended to facilitate implantation of the prosthesis, as will be explained hereinafter.

The outer surface of the covers 306 has irregularities, for example formed by embossing or sintering, which are intended to guarantee good stability of the prosthesis once it has been fitted. At their anterior end, the covers 306 are provided with tabs 322 projecting towards one another so as to overlap partially when the prosthesis is in the free state. As a result of the extension 318, one of these tabs 322A is further from the posterior end of the prosthesis than the other tab 322B. For the sake of clarity, these tabs 322A, 322B will therefore be referred to as distal tab and proximal tab, respectively.

Each of these tabs is provided with a respective opening 324A, 324B of substantially circular cross section. The position of these openings is such that they are mutually aligned in the longitudinal direction of the prosthesis and coaxial to the orifice 320 when the prosthesis is in a transversely compressed state, as will be described in particular with reference to FIG. 15. The cover provided with the distal tab 322B ends with a projection 326 extending beyond this tab, away from the core 304. This projection 326 constitutes an abutment for the distal tab 322A, in such a way as to limit the overall flexion movement of the anterior part of the prosthesis.

FIG. 14 shows an instrument, designated in general by reference number 328, and intended for implanting the prosthesis shown in FIGS. 11 to 14.

This instrument 328 comprises first and second movable elements 330, 332. The first element 330 is made up of a cylindrical shaft 334 assuming the function of grip handle, ending with two tongues 336 with a cross section in the shape of an arc of a circle, intended to bear against the edges of the covers of the prosthesis, as will be described hereinafter. The shaft 334 is hollow and annular and comprises a cylindrical axial seat 338.

The second element 332 is made up of a cylindrical rod 340 ending with a thinned end 342 which is intended to form a wedge, the function of which will be explained in particular with reference to FIGS. 16 and 17. The main transverse dimension, or width 1, of this end 342 decreases away from the rod 340. The rod 340 is continued, away from its end 342, via a widened cylindrical portion 344 fitting in the seat 338 of the shaft 334. This fitting portion 344 itself ends with a grip 346. The rod 340 and the fitting portion 344 are free to slide relative to the shaft 334 and to pivot about the main axis of the latter.

Figure 15:
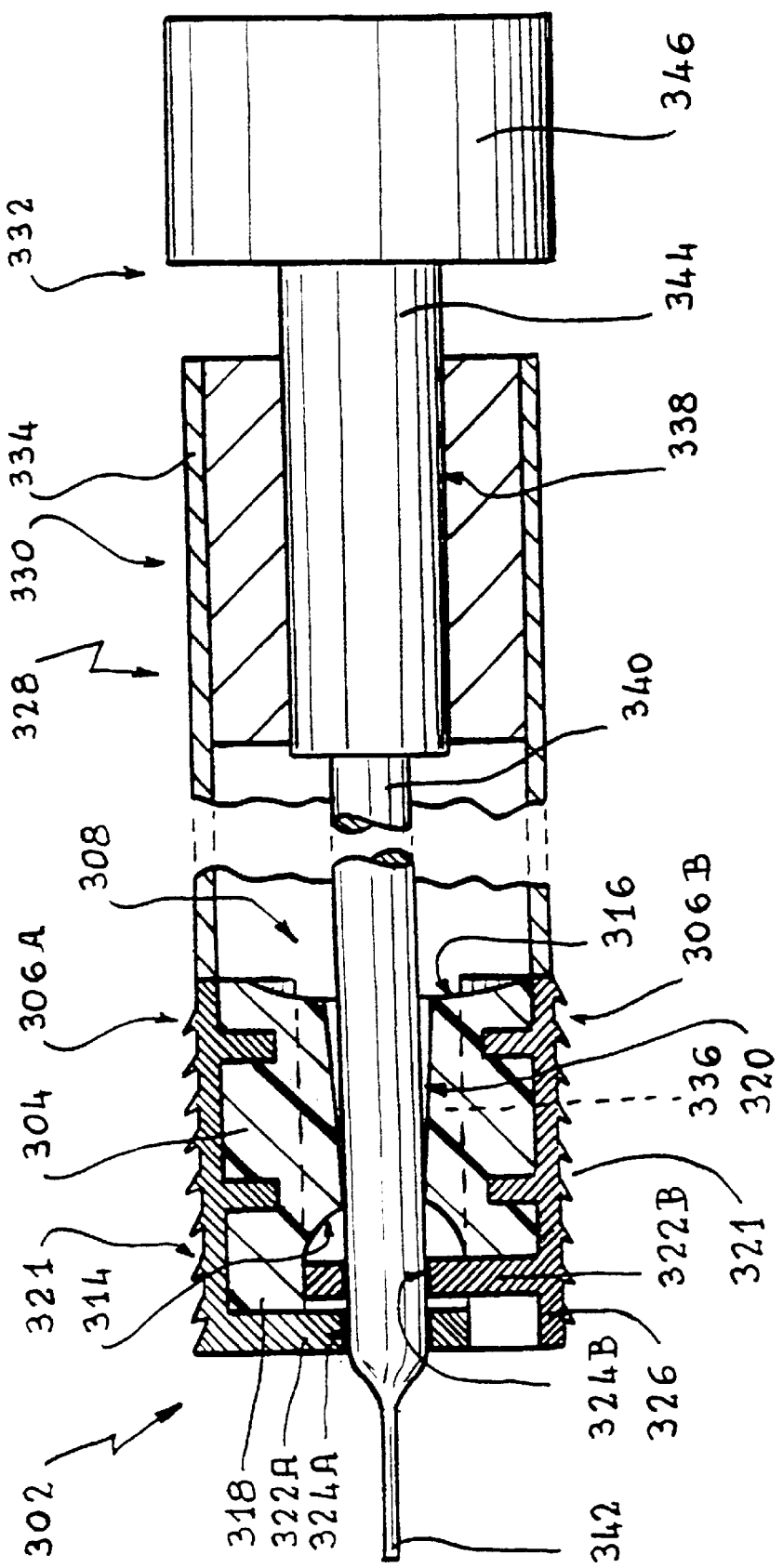
FIG. 15 is a longitudinal section illustrating the connection of the implantation instrument in FIG. 4 to the prosthesis in FIGS. 11 to 13.
Figure 18:
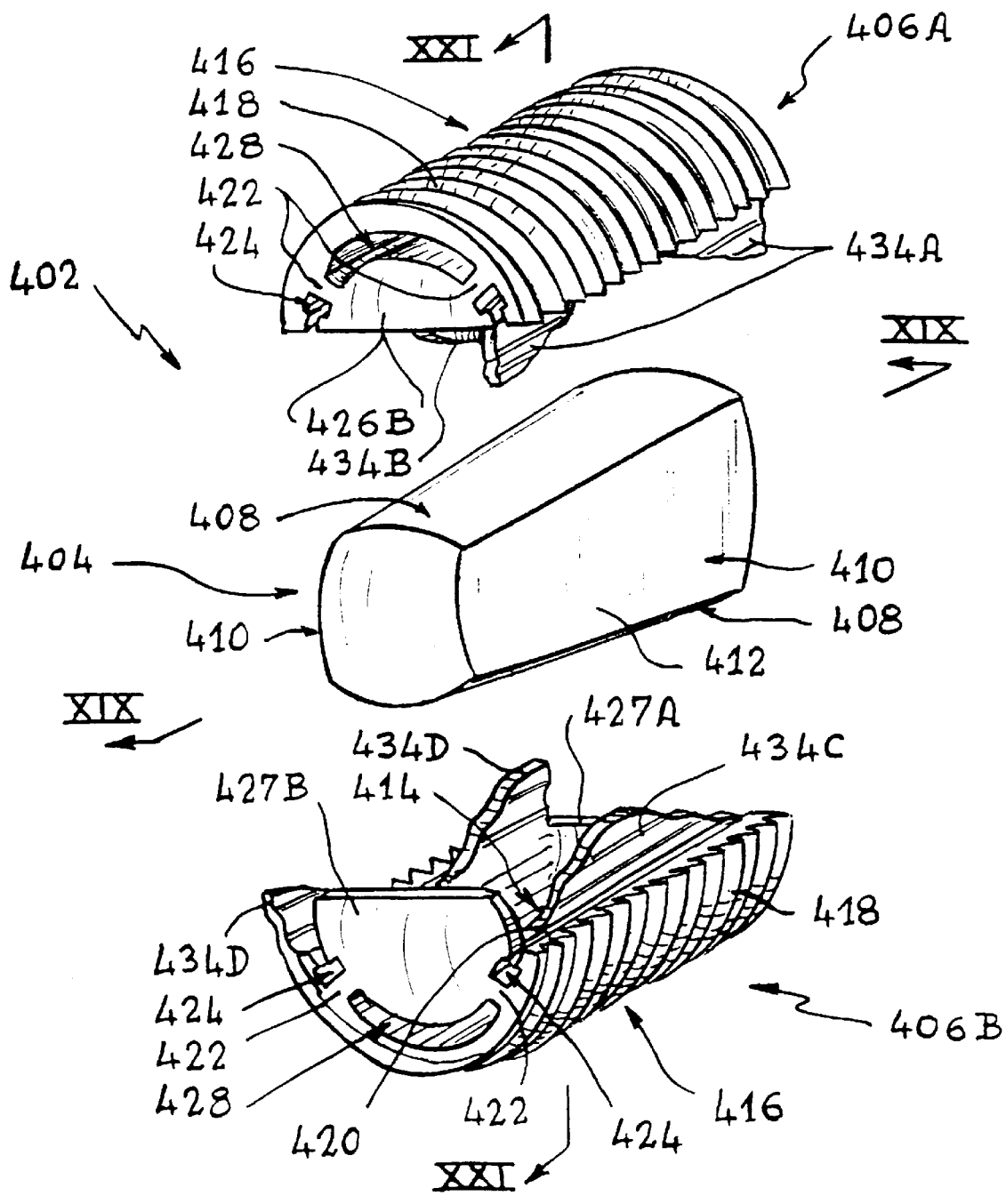
FIG. 18 is a perspective view of a fifth embodiment of a disc prosthesis according to the invention.

FIG. 15 illustrates the mutual fastening of the implantation instrument 328 and the prosthesis 302. For this purpose, it is necessary first to insert the rod 340, then the fitting portion 344 into the annular seat 338. The prosthesis 302 is then compressed so that it has a generally cylindrical cross section. Such compression can be achieved manually, for example, or by means of a suitable clamp.

The rod 340 is then introduced via its thinned end 342 through the orifice 320, then into the two openings 324A, 324B arranged in the continuation of each other. The insertion of this rod 340 thus ensures attachment of the prosthesis 302 and the implantation instrument 328 in the transversely compressed state of the prosthesis. At the same time as the rod 340 is being inserted into the openings 324A, 324B, the shaft 334 is moved longitudinally so that the tongues 336 bear against the edges of each cover 306A, 306B, so as to form, with the outer surface of the prosthesis, a generally cylindrical surface.

The prosthesis is implanted in the patient's body by screwing by means of an action exerted on the shaft 334 which acts as a handle. The threadings 321 provided on the outer periphery of the covers 306 are advantageous with regard to this operation. Once the prosthesis is in place, a longitudinal force is exerted tending to withdraw the rod 340 from the openings 324A, 324B, so that the prosthesis assumes a configuration widening towards its anterior part on account of the nature of the prestressed material from which it is made. The tongues 336 are then withdrawn by sliding.

FIG. 16 shows the mutual position of the tabs 322A, 322B once the prosthesis 302 has been implanted in the patient's body. The prosthesis is then in an intermediate state of compression between its free state shown with reference to FIGS. 11 to 13 and its compressed state for implantation, shown in FIG. 15.

This is because the vertebrae between which it is arranged exert a certain force on this prosthesis, which force, however, is less than that to which it is subjected during implantation. Viewed from the end, there is therefore an overlap zone Z between the openings 324A, 324B provided on the tabs 322A, 322B. The presence of this overlap zone is particularly advantageous in the case where one wishes to remove the prosthesis, particularly in the case of loosening or infection.

For this purpose, the rod 340 and the fitting portion 334 are introduced into the shaft 344, then the end 342 of this rod 340 is inserted into this overlap zone Z. Given that the width 1 of the end 342 increases towards the rod 340, the lateral walls of this end 342 come into abutment, upon introduction, against the circumference of the overlap zone, as is shown in FIG. 16. A quarter turn is then effected by means of the grip 346 integral with the rod 340, so as to bring the openings 324A, 324B together, as is shown in FIG. 17. The converging design of the end 342 allows the latter to adapt to overlap zones of different dimensions.

Finally, an axial thrust is applied to the rod 340 in order to engage the cylindrical body of the rod 340 in the openings 324A, 324B. The prosthesis is then in the same transversely compressed state as during its implantation, illustrated in FIG. 15.

The tongues 336 are engaged in an analogous manner along the edges of the covers 306. It is then possible to unscrew the prosthesis 302 so as to remove it from the patient's body. The prosthesis 302 illustrated in FIGS. 15 to 17 is a posterior prosthesis, given that its implantation is performed from the patient's back and that it is intended to replace the posterior part of the disc.

However, such a prosthesis 302 can also be implanted from the anterior aspect of the patient in order to be placed in the anterior part, or the antero-median part, of the intervertebral space. This implantation differs from that described above solely in the sense that, to connect the rod 340 to the prosthesis 302, it is necessary to introduce this rod first through the openings 324A, 324B of the prosthesis, then into the orifice 320 of the latter.

The prosthesis 302 has been shown with end portions 308 whose transverse dimension is substantially constant along the whole length of this prosthesis. It is also possible for these ends, while still having a substantially constant radius of curvature along the whole length of this prosthesis, to extend about an angular sector which increases continuously towards the anterior part of the prosthesis.

FIGS. 18 to 22 show a fifth embodiment of a partial disc prosthesis according to the invention, designated in general by reference number 402. This prosthesis comprises a core 404 which is made of a biocompatible elastic material and whose outer surface is partially covered by means of a casing made up of two elements 406A and 406B. These elements, made of a biocompatible rigid material, are attached to the core 404 by means of a silicone adhesive, for example.

The cross section of the core 404 is made up of two end portions 408 whose outer periphery describes an arc of a circle, and which are connected via two flat surfaces 410 forming a middle part 412.

The transverse dimension or width of the end portions 408 is substantially constant along the whole length of the prosthesis 402, while the height of the flat surfaces 410 increases towards the front of the prosthesis, referring to the prosthesis once it has been implanted.

Each casing 406 comprises a central cap 414 intended to come into contact with the core 404. This cap 414 is connected to a peripheral cover 416 made in the form of a profiled part having, in cross section, the shape of an arc of a circle. The outer surface of these covers is provided with a threading 418 intended to facilitate the implantation of the prosthesis.

The connection zone between the cap 414 and the cover 416 comprises a peripheral edge 420 extending around the cap and continued via two longitudinal brackets 422. The latter define, near the edge 420, two longitudinal slides or grooves 424. These brackets 422 also delimit, with end flaps 426, a transverse notch 428 in the shape of an arc of a circle.

Four flaps are provided, namely front flap 426A and rear flap 426B for the casing 406A, and front flap 427A and rear flap 427B for the casing 406B.

Each flap 426, 427 extends from one of the casings 406 towards the one opposite it and does so in a manner substantially perpendicular to the main axis of the prosthesis. These flaps are arranged asymmetrically.

The front flap 426A of the first casing 406A and the opposite flap, namely the rear flap 427B of the other casing 406B, extend, along their main dimensions, in such a way as to form an overlap zone ZR. The latter can be seen in particular in FIG. 21. The continuations of the flaps 426A and 427B on the same plane, along the main axis A of the prosthesis, have a common region which forms the overlap zone ZR. The presence of the latter is such as to reduce the antero-posterior shearing to which the prosthesis 402 is subjected once it has been implanted.

Figure 19:
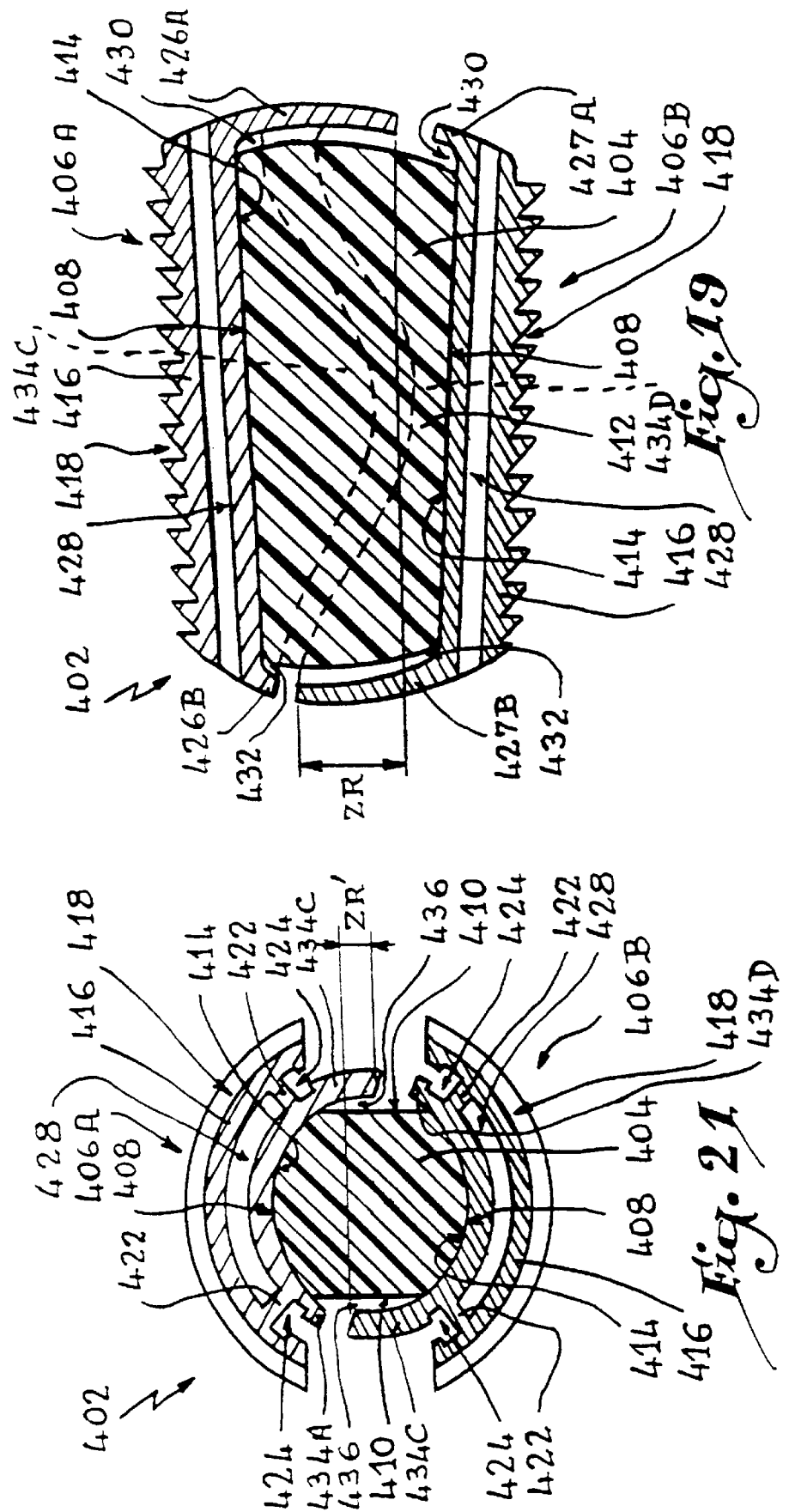
FIGS. 19 and 20 are longitudinal sections along the line XIX—XIX in FIG. 18, in rest and compression positions, respectively, of the prosthesis in this FIG. 18.

As is shown in FIG. 19, each flap 426, 427 extends, in the uncompressed rest position of the prosthesis, a distance from the opposite wall of the core 404. This contributes to forming longitudinal differential volumes, namely a front volume 430 and a rear volume 432 respectively, which limit the expansion of the prosthesis during its compression.

Figure 20:
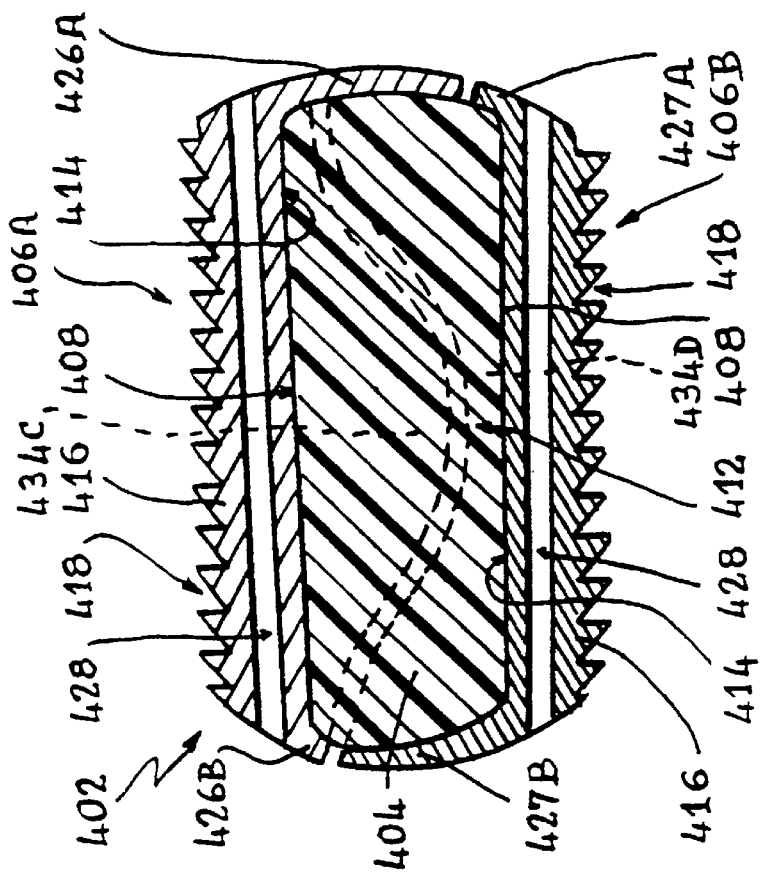
Figure 22:
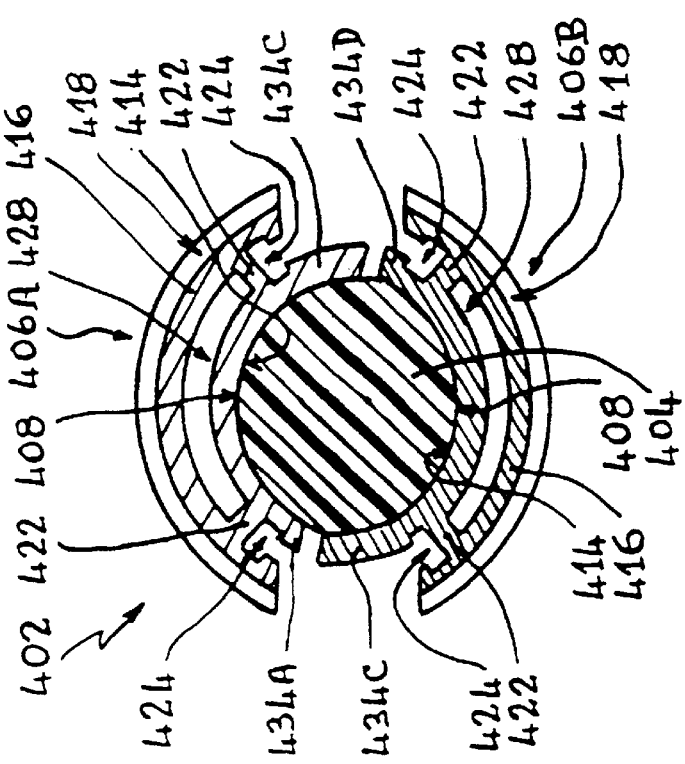

This is shown more particularly in FIG. 20 which illustrates the position of maximum compression of the prosthesis. In this position, the walls of the core 404, which were distant from the flaps 426 in the rest position, come to bear against the inner face of these flaps. In this compressed position, the opposite flaps, namely on the one hand 426A, 427A and on the other hand 426B, 427B, are distant from one another.

Each casing 406 is also provided with lateral skirts 434 extending from the peripheral edge 420 between each slide 424 and the cap 414. As is shown in particular in FIG. 19, each skirt 434 has, in side view, a variable height, extending as it does along a generally sinusoidal undulating profile. However, each skirt can also include at least one set-back. The adjacent skirts provided on two different casings have substantially conjugate profiles. Thus, the skirts 434A and 434C on the one hand and the skirts 434B and 434D on the other hand are able to interlock with each other.

By contrast, two facing skirts, that is to say either 434A and 434B or 434C and 434D, are arranged asymmetrically. There are therefore overlap zones ZR' on the one hand between the opposite skirts 434A and 434D and on the other hand between the opposite skirts 434B and 434C. The continuations of each couple of opposite skirts on the same plane, along an axis perpendicular to the main axis of the prosthesis, have common regions which form these overlap zones. These contribute to reducing the lateral shearing effects to which the prosthesis is subjected.

In cross section, as is shown in particular in FIG. 21, each skirt 434 extends a distance from the flat surfaces 410 of the core 404. This contributes to creating, on either side of the core 404, two lateral differential volumes 436. Upon maximum compression of the prosthesis, shown in FIG. 22, the core 404 occupies both of these differential volumes 436, in such a way as to come into contact with the inner face of the skirts 434. In this compressed position, it should be noted that the ends of the adjacent skirts, on the one hand 434A and 434C and on the other hand 434B and 434D, extend a distance from one another.

The prosthesis illustrated in FIGS. 18 to 23 is implanted using an instrument which is substantially analogous to that 22 described in FIGS. 4 to 8. The adjacent slides, namely on the one hand 424A and 424C and on the other hand 424B and 424D, permit engagement of tongues analogous to those 28 in FIGS. 4 to 8. The instrument is also provided with supplementary tongues, not shown in these FIGS. 4 to 8, penetrating into the two notches 428 provided on the casings 406. The fitting of the prosthesis 402 is in general analogous to that of the prosthesis 2, illustrated with reference to FIGS. 1 to 8.

Figure 23:
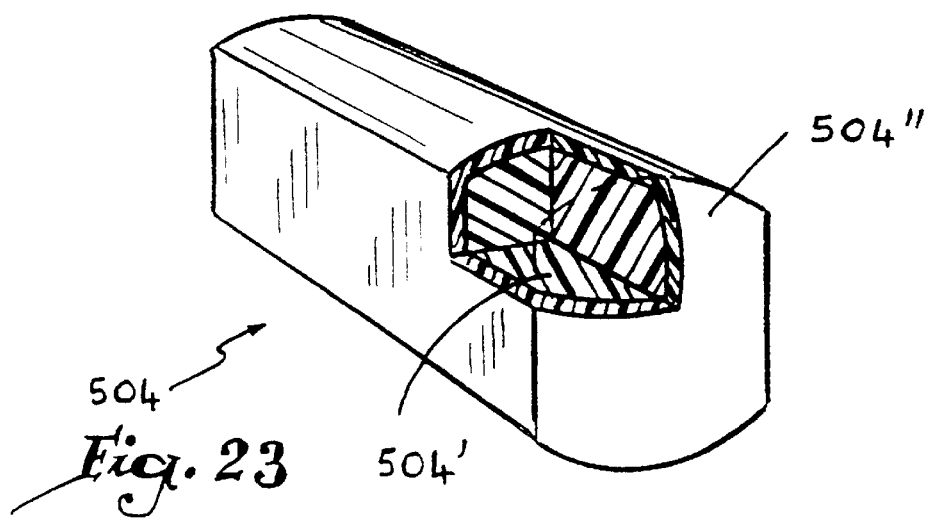
FIG. 23 is a perspective view, with part cut away, of a composite core of a prosthesis according to the invention.

FIG. 23 illustrates a core, designated in general by reference number 504, capable of replacing the core of a prosthesis described above. This core 504 is composite, that is to say it comprises a centre 504' surrounded by an envelope 504", the material of the centre 504' being more compressible than that of the envelope 504". By way of non-limiting example, the centre is made of a silicone polymer while the envelope 504" is made of polyethylene or polyurethane.

This centre 504' occupies a substantial part of the volume of the core 504 and is surrounded by the envelope over its whole periphery. It is possible for the centre, made of a compressible material, to be separated from the outer envelope by a succession of intermediate linings, the materials of which have alternating characteristics of compressibility.

It is also possible for the core to be made in the form of a centre consisting of a more compressible material, surrounded by an envelope consisting of a less compressible material. This centre will then extend uniquely in the rear part of the prosthesis, the transverse dimensions of which are reduced.

The use of a composite core is advantageous in the sense that it limits the expansion of this core and prevents the phenomenon of hernias.

Figure 24:
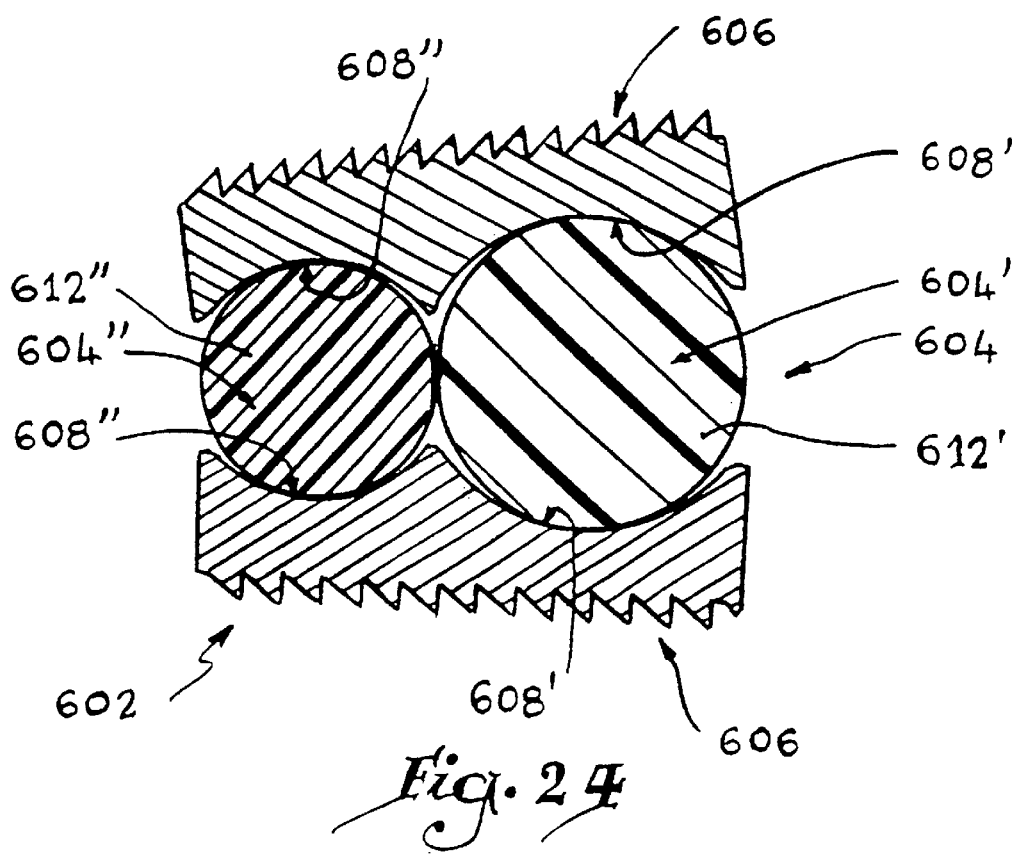
FIG. 24 is a longitudinal section of a core made up of several elements belonging to a prosthesis according to the invention.

FIG. 24 illustrates a supplementary embodiment in which the core 604 comprises several separate elements, namely a front element 604' of greater transverse dimensions, and a rear element 604" of restricted transverse dimensions. The terms "front" and "rear" relate to the prosthesis once implanted. The front element 604' is made of a more compressible material than the rear element 604". Each element, the front one 604' and the rear one 604", respectively, comprises two transverse end portions 608', 608" connected via respective middle portions 612', 612".

The two end portions of the same element are arranged in a generally symmetrical manner with respect to a middle plane of the prosthesis which corresponds substantially to the plane of the intervertebral disc. Each end portion 608', 608" is covered by a casing forming a threaded cover 606, the inner wall of which is designed in such a way as to hold the front and rear elements in place. This prosthesis can be provided with a casing analogous to the one covering the prosthesis in FIGS. 18 to 22.

With the prosthesis according to the invention it is possible to achieve the objects which were set out. Indeed, the design of its end portions in the shape of an arc of a circle and the presence of rigid covers provided with an outer threading ensure straightforward implantation by screwing. The fact that the prosthesis has greater transverse dimensions at its front part than at its rear part confers upon it a lordosis appearance which is found to be advantageous from a physiological point of view. The presence of a recess in the front part, or even in the rear part, of the prosthesis allows its transverse dimensions to be modified as a function of the forces to which it is subjected, and this gives great freedom of movement to the patient receiving it.

The irregularities in the outer surface of the covers guarantee good stability of the prosthesis, both by friction on the vertebrae and on account of the bone regrowth which may occur there.

The fact that a cover extends beyond the anterior end of the core (FIG. 9) leads to the creation of a leverage which, combined with the presence of the recesses, ensures particularly easy flexion of this anterior part of the prosthesis.

The presence of an abutment limiting the movement of the upper cover additionally reduces the risks of posterior expulsion of the prosthesis.

The implantation of the prostheses shown in all the figures is particularly easy. Indeed, given that the prosthesis is able to undergo a substantial reduction of its transverse dimensions, it can be implanted easily without damaging the organs around which it is moved. Moreover, the mutual connection and disconnection of the prosthesis and the implantation instrument, which are effected by longitudinal sliding, permit easy engagement of the prosthesis relative to the implantation instrument. This mode of connection also guarantees easy removal of the implantation instrument from the prosthesis, once the latter has been implanted. Given that the implantation instrument is removed longitudinally, there is therefore only a slight risk of damaging the organs around which the instrument is manoeuvred.

The presence of tabs in which openings are formed, providing an overlap zone once the prosthesis has been implanted, is particularly advantageous. The reason is that, by means of insertion of the wedge-forming end of the rod (FIG. 17), this overlap zone makes it possible to compress the prosthesis even when direct access to the latter is impossible for the surgeon. This measure thus provides the possibility of removing the prosthesis without undermining the physical integrity of the patient.

The use of flaps and/or skirts defining, with the facing walls of the core, a differential volume of expansion of the core is also advantageous. This makes it possible to give the prosthesis according to the invention three different stages of compression. In a first stage, referred to as low charge, the prosthesis does not substantially deform. In a second stage, referred to as medium charge, the elastic core deforms so as to occupy all of these differential volumes. Finally, in a third stage, referred to as high charge, the prosthesis is substantially rigid, given that the core comes into contact, without being able to be substantially deformed, with the walls of the skirts and/or flaps defining these differential volumes.

What is claimed is:

1. Partial disc prosthesis (2; 102; 202; 302; 402; 602) intended to be inserted between two adjacent vertebrae, of the type comprising a core (4; 104; 204; 304; 404; 504; 604) made of an elastic material comprising a silicone polymer or an elastomer, covered, over part of its periphery, by a casing (6; 106; 206; 306; 406; 606) made of a rigid material and intended to be in contact with the said two adjacent vertebrae, characterized in that the said core comprises, in cross section, two end portions (8; 108; 308; 408; 608', 608"), connected by a middle portion (12; 138; 312; 412; 612', 612"), the said casing comprises two covers (6; 106; 206; 306; 416; 606) provided with a threading and respectively covering, at least partially, the outer periphery of the said end portions (8; 108; 308; 408; 608', 608"), and the distance separating the said covers increases towards the anterior part of the prosthesis.

2. Prosthesis according to claim 1, characterized in that the core (4; 104; 204; 304; 404; 504) is made in one piece and has an elongate shape.

3. Prosthesis according to claim 1, characterized in that the core (604) comprises several elements (604', 604").

4. Prosthesis according to claim 3, characterized in that the core (604) comprises a rear element (604") and a front element (604') which is more compressible than the rear element and whose transverse dimensions are greater than those of the rear element.

5. A disc prosthesis to insert between two adjacent vertebrae, comprising:

a core comprised of one or more elastic materials, said core including a pair of end portions;

a casing at least partially enclosing said core, said casing including two rigid covers positioned opposite one another, said core being positioned between said covers, said covers each including threading and being arranged with a distance separating said covers that increases from one of said end portions to another of said end portions.

6. The prosthesis of claim 5, wherein said core is comprised of at least a rear element and a front element, said front element being more compressible than said rear element.

7. The prosthesis of claim 5, wherein said end portions are substantially in the shape of a circle.

8. The prosthesis of claim 1, wherein one of said end portions of said core is shaped to define an incipient flexion recess.

9. The prosthesis of claim 1, wherein said core includes a middle portion having two flat surfaces connecting said end portions.

10. The prostheses of claim 1, wherein said covers each include one or more longitudinal grooves.

11. The prosthesis of claim 1, wherein said core includes a center comprised of a first material contained within an envelope comprised of a second material, said second material being less compressible than said first material, said first material and said second material belonging to said one or more materials.

12. The prosthesis of claim 1, wherein at least one of said covers extends beyond one of said end portions.

13. The prosthesis of claim 1, further comprising an abutment projecting from a first one of said covers toward a second one of said covers, said abutment being operable to limit movement of said second one of said covers in the direction of the said first one of said covers.

14. The prosthesis of claim 1, further comprising:

means for reducing antero-posterior shearing;

means for reducing lateral shearing; and wherein said casing includes a cap in contact with said core separated from said covers by an indented connection zone.

15. The prosthesis of claim 1, wherein said casing includes a first tab extending from a first one of said covers and a second tab extending from a second one of said covers, said first tab defining a first opening and said second tab defining a second opening, said first opening being configured to align with said second opening when said core is compressed between said covers.

16. An apparatus, comprising:

a disc prosthesis arranged to be placed between two adjacent vertebrae, said prosthesis including a core comprised of one or more elastic materials, said core including a pair of end portions and a casing at least partially enclosing said core, said casing including two rigid covers positioned opposite one another, said core being positioned between said covers, said covers each including threading and being arranged with a distance separating said covers that increases from one of said end portions to another of said end portions; and implantation instrumentation including a rod and a handle connected to a pair of opposing tongues, said tongues being configured to selectively engage said covers and said handle defining an orifice to receive a rod therethrough to selectively contact said disc prosthesis.

17. The apparatus of claim 16, wherein said covers each include one or more grooves and said tongues each include one or more ribs, said one or more ribs each being operable to slidably engage a corresponding one of said one or more grooves.

18. The apparatus of claim 16, wherein said casing includes a first tab extending from a first one of said covers and a second tab extending from a second one of said covers, said first tab defining a first opening and said second tab defining a second opening, said first opening being configured to align with said second opening when said core is compressed between said covers, and said rod of said implantation instrumentation is configured to pass through said first opening and said second opening when aligned.

19. The apparatus of claim 16, wherein said core includes a longitudinal orifice sized to receive said rod of said implantation instrument.

* * * * *